(12) United States Patent
Schouenborg

(10) Patent No.: US 8,306,632 B2
(45) Date of Patent: Nov. 6, 2012

(54) DISSOCIATING MULTI-CHANNEL ELECTRODE

(75) Inventor: Jens Olaf Roe Schouenborg, Lund (SE)

(73) Assignee: Neuronano AB, Karlshamn (SE)

( * ) Notice: Subject to any disclaimer, the term of this patent is extended or adjusted under 35 U.S.C. 154(b) by 709 days.

(21) Appl. No.: 11/950,942

(22) Filed: Dec. 5, 2007

(65) Prior Publication Data

US 2008/0177363 A1    Jul. 24, 2008

Related U.S. Application Data

(60) Provisional application No. 60/897,034, filed on Jan. 23, 2007.

(30) Foreign Application Priority Data

May 14, 2007 (SE) ...................................... 0701150

(51) Int. Cl.
*A61N 1/34* (2006.01)
(52) U.S. Cl. ...................................................... 607/117
(58) Field of Classification Search ........... 607/115–117
See application file for complete search history.

(56) References Cited

U.S. PATENT DOCUMENTS

| | | | |
|---|---|---|---|
| 5,366,493 A | | 11/1994 | Scheiner et al. |
| 5,658,327 A * | | 8/1997 | Altman et al. ................ 607/127 |
| 5,931,864 A | | 8/1999 | Chastain et al. |
| 6,080,160 A | | 6/2000 | Chen et al. |
| 6,597,953 B2 * | | 7/2003 | Boling ............................ 607/45 |
| 6,613,378 B1 | | 9/2003 | Erhan et al. |
| 7,209,788 B2 * | | 4/2007 | Nicolelis et al. ................ 607/48 |
| 2002/0035388 A1 * | | 3/2002 | Lindemans et al. .......... 607/120 |
| 2003/0158545 A1 * | | 8/2003 | Hovda et al. .................... 606/32 |
| 2004/0199235 A1 * | | 10/2004 | Younis .......................... 607/116 |
| 2005/0131508 A1 * | | 6/2005 | Garabedian et al. .......... 607/122 |
| 2005/0137672 A1 * | | 6/2005 | Coe et al. ...................... 607/126 |
| 2006/0155343 A1 * | | 7/2006 | Vilims ........................... 607/43 |
| 2007/0088417 A1 | | 4/2007 | Schouenborg |

FOREIGN PATENT DOCUMENTS

| WO | WO-03028521 A2 | 4/2003 |
|---|---|---|
| WO | WO-03086502 A2 | 10/2003 |
| WO | WO-2007040442 | 4/2007 |

OTHER PUBLICATIONS

William D. Memberg, et al. An Analysis of the Reliability of Percutaneous Intramuscular Electrodes in Upper Extremity FNS Applications IEEE Transactions on Rehabilitating Engineering vol. 1 No. 2, Jun. 1993.

* cited by examiner

*Primary Examiner* — Rex R Holmes
(74) *Attorney, Agent, or Firm* — Dickstein Shapiro LLP

(57) ABSTRACT

An electrode array for insertion into soft tissue comprises a multitude of thin flexible electrodes each having a distal tip and a proximal end, wherein at least portions of the electrodes extending from their proximal ends are disposed in parallel. The electrodes are embedded in a matrix dissolvable in an aqueous solvent such as a body fluid. The matrix comprises two or more sections differing in their dissolution rates. A first section encloses a portion of the electrodes extending in a proximal direction from a distal portion thereof. A second section encloses a portion of the electrodes extending from the first section towards their proximal ends.

19 Claims, 11 Drawing Sheets

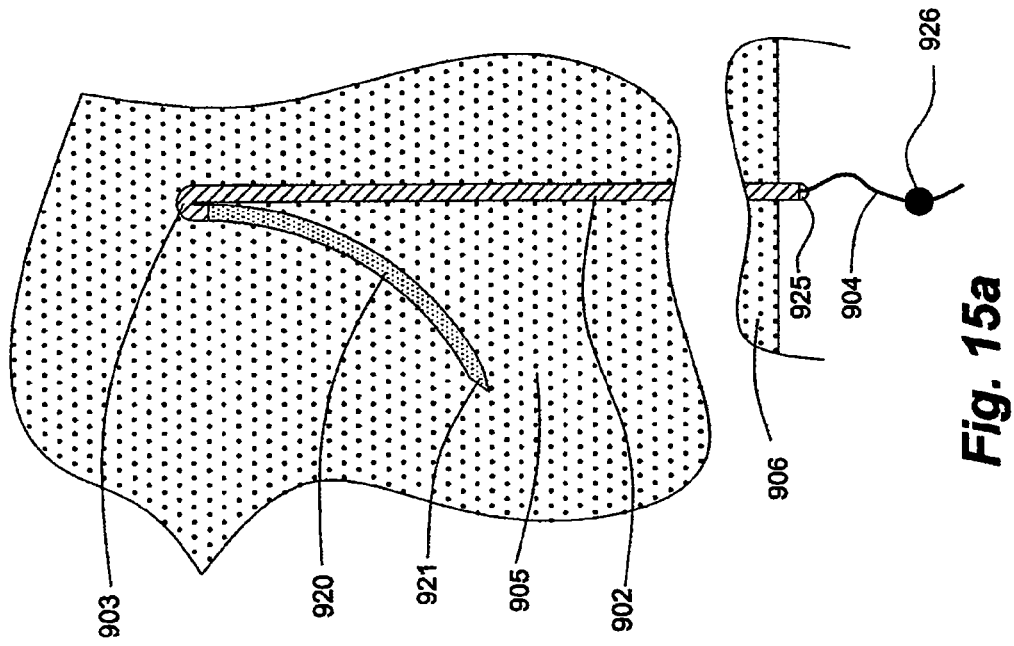
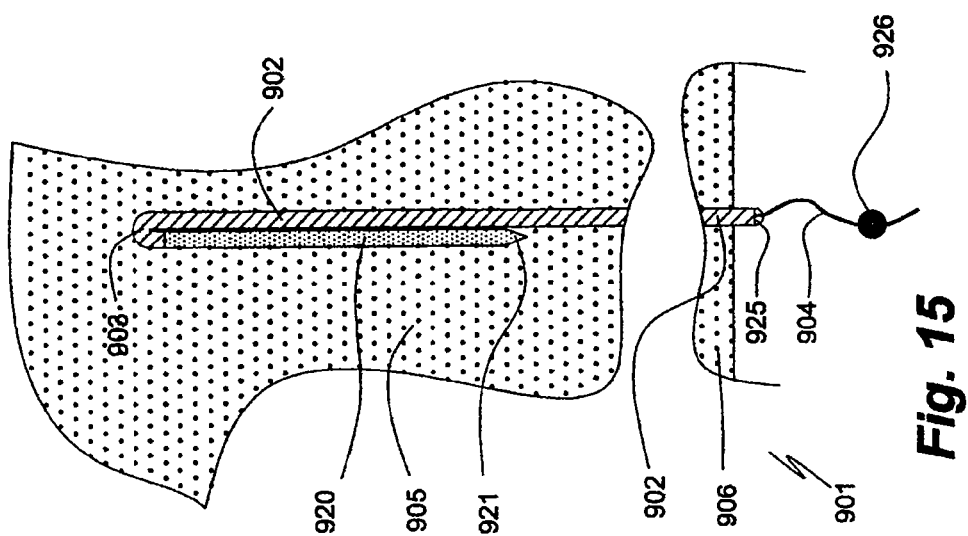

DISSOCIATING MULTI-CHANNEL ELECTRODE

FIELD OF THE INVENTION

The invention relates to a medical electrode array for insertion into soft tissue such as the brain, the spinal cord, endocrine organs, muscles, and connective tissue, comprising a multitude of thin wire electrodes, to a method of its manufacture, and to uses of the electrode array.

BACKGROUND OF THE INVENTION

Electrodes that can be implanted for a long time into the central nervous system (CNS) have a wide field of application. In principle, all brain and spinal cord tissue can be recorded from or stimulated by such electrodes and their functions monitored and controlled. Stimulation of the brain or spinal cord can be of particular value in situations when brain nuclei are degenerated or injured. Monitoring brain activity can be useful if linked to drug delivery or other measures such as electrical stimulation. Electrodes can also be used to lesion specific sites in tissue. To record and stimulate brain structures various forms of implanted electrodes have been developed and used in the past. The use of multiple electrodes for such purposes in form of electrode arrays is desirable. A suitable electrode array or bundle is known from WO 2007/040442 A1, which is incorporated in this application by reference. In regard of this and other known electrode arrays it is desirable to improve the freedom of movement of individual electrodes and their positioning in soft tissue.

OBJECTS OF THE INVENTION

One object of the invention is to provide an electrode array of the aforementioned kind, individual electrodes of which are gaining in freedom of movement in respect of each other after the electrode array has been inserted into soft tissue.

Another object of the invention is to provide an electrode array of the aforementioned kind, which can be easily positioned in a desired location in soft tissue and there anchored.

An additional object of the invention is to provide an electrode array of the aforementioned kind that is retained in a chosen location in soft tissue over an extended period of time and that is not easily displaced by corporal movements of the person into which the electrode is implanted.

Still another object of the invention is to provide an electrode array of the aforementioned kind that is easy to manufacture.

Further objects of the invention will become evident from a study of a short description of the invention, a number of preferred embodiments illustrated in a drawing, and of the appended claims.

SUMMARY OF THE INVENTION

The electrode array of the invention comprises a multitude of electrically conductive thin flexible, preferably resiliently flexible, electrodes embedded in a solid matrix that is dissolvable and/or degradable in an aqueous environment, such as in living tissue. The electrode array of the invention is intended for insertion into soft living tissue, in particular brain and spinal cord tissue, but also, for instance, into the liver, the kidneys or connective tissue. Once inserted, the matrix holding the electrodes is dissolved and/or degraded. The matrix acts as a glue or an adhesive keeping the electrodes in fixed positions in respect of each other until dissolved and/or degraded upon insertion of the electrode array into tissue. This makes the electrode array to be transformed to a multitude of individual electrodes, which are no longer restrained by the matrix from moving in respect of each other. On the other hand, the disposition of the electrodes in the tissue will reflect, at least to some extent, their spatial relationship in the electrode array.

The electrode array of the invention is preferably generally symmetric in respect of a central axis thereof. The oblong electrode array of the invention has a distal end and a proximal end. In this application, "distal" refers to a portion of the electrode array that is further away from the person inserting the electrode array into tissue than a proximal portion thereof, and also to a direction of movement away from said person. At least proximal portions of the electrodes are disposed in parallel or about in parallel with the central axis. The electrode array of the invention can be of any suitable form, such as of circular, elliptic or substantially flat form in a transverse section in respect of the central axis. The central axis generally coincides with the axis of insertion of the electrode array into tissue. Distal terminal portions (front end portions) of all or some electrodes in an electrode array are disposed in parallel or in a configuration in which at least some of the electrodes are fanning out from the central axis or comprise fanning-out means operative upon dissolution and/or degradation of a matrix portion enclosing them by displacement of the electrode array in tissue in a distal direction The electrodes of the invention are preferably insulated except for at portions extending from their proximal and distal ends. The distal ends or tips of the electrodes, which are not insulated, can be of any suitable shape. Suitable shapes, in particular barbed tips, are disclosed in WO 2007/040442. At its proximal end, each electrode is in electrically conductive contact with electronic equipment, preferably via a multi-lead flexible cable. This allows the individual electrodes to be addressed separately or in groups.

The electrodes of the invention can be used for recording and/or for nerve-stimulating purposes. If used for recording purposes, an electrode of the invention can be equipped with a miniaturized preamplifier to improve the signal to noise ratio, the preamplifier being wire-connected to a main amplifier.

The electrodes of the invention are preferably provided with anchoring means, such as barbs, rough surface portions or surface portions having adhesive properties in respect of surrounding tissue. It is preferred for the barbs to function as electrode tips in which case they are not insulated. It is also preferred for the electrodes of the invention to be of varying length and to be arranged in the electrode array around a central axis thereof with the longest electrodes at a short distance from the axis, the shortest electrodes at a longer distance from the axis, and the electrodes of intermediate length at intermediate distances from the axis so as to make their distal tips define an electrode array tip while their proximal ends are preferably disposed in a plane transverse to the axis. It is however also within the scope of the invention to arrange the electrodes in a manner forming a unilaterally slanting or otherwise not symmetric electrode array tip.

According to a preferred aspect of the invention the electrode array comprises one or more optical fibers to provide for radiative stimulation of the tissue or components thereof and/or for recording radiation emanating from surrounding tissue. In a manner corresponding to that of the electrodes the one or more optical fibers are kept in a selected position in the array by means of the matrix.

According to another preferred embodiment the electrode array comprises one or more contractile bimetallic elements that change their shape, for instance bend, when electric current is passed through them. Alternatively one or more contractile polymer elements comprised by the electrode array can be used to control its path of insertion.

According to a third preferred aspect of the invention the electrode array comprises a distal terminal portion extending from the distal end and a main portion extending in a proximal direction from the distal terminal portion. It is preferred for the distal terminal portion to be tapering in a distal direction so as to form, for instance, a conical or flat triangular terminal distal portion. For some applications, the terminal distal portion can have a blunt shape to minimize the risk of vascular ruptures during insertion of the electrode array.

According to a fourth preferred aspect of the invention the matrix comprises two or more sections differing in their dissolution and/or degradation rates in soft tissue, in particular a first section comprised by the distal terminal portion and a second section comprised by the main portion of the electrode array and extending in the direction of the proximal end thereof, optionally to the proximal end so as to embed the proximal end therein. Optionally a short length of the distal electrode portion including electrode tip can extend distally or in an oblique distal direction from the first matrix section. It is preferred for the dissolution rate of the first matrix section to be substantially higher than the dissolution and/or degradation rate of the second matrix section but other solution/degradation rate relationships of the first and second matrix sections are also comprised by the invention. On insertion of the electrode array into the target tissue, such as soft tissue of the brain, the first and second matrix portions come into contact with body fluid and are subsequently dissolved and/or degraded by this contact, the dissolution/degradation rate of the first portion being substantially greater than the dissolution/degradation rate of the second portion. It is preferred for a matrix section to comprise a dissolution/degradation enhancing means such as channels that can be infiltrated by body fluid. Thus it is preferred for a matrix section to have a porous structure. An electrode comprising two or three axially joining matrix sections, in particular two matrix sections, is preferred. It is preferred for a matrix section to comprise or to consist of a carbohydrate and/or a protein.

For insertion of the electrode array into soft tissue a manually operated or other micromanipulator is attached or attachable to a proximal end portion of the electrode array, from which it extends in a proximal direction.

The relative stiffness of the combination of electrodes and matrix of the electrode array provides for its easy insertion into tissue. Upon insertion, the first, distal matrix section is quickly dissolved. Thereby the distal terminal portion of an electrode becomes capable of lateral displacement in respect of neighboring electrodes. Further insertion of the electrode array into the tissue causes distal portion of an electrode comprising a fanning-out means to bend in a direction generally away from the axis of the electrode array in an unfolding manner. Dissolution and/or degradation of the second matrix portion frees the proximal portion of an electrodes so that it becomes capable lateral and/or axial displacement in relation to neighboring electrodes and to assume a floating disposition in the tissue; thereby its position in the tissue is stabilized and tissue reactions/injuries that otherwise would have occurred due to its joint movement with other electrodes be prevented.

According to a fifth preferred aspect of the invention the electrode array comprises an insertion element, such as a contact element comprised by a micromanipulator, attached to its proximal end and extending from that end in a proximal direction. It is preferred for the insertion means to be attached to the electrode array by an adhesive that is dissolvable in an aqueous environment. It is preferred for the adhesive to dissolve substantially more rapidly in body fluid than the material of the second matrix portion. Thereby the electrode array is automatically separated from the micromanipulator at a selected point in time upon insertion into tissue, allowing the micromanipulator to be withdrawn.

According to a sixth preferred aspect of the invention two or more electrode arrays disposed in parallel can be joined by a dissolvable connecting layer or layers disposed between matching surfaces thereof.

According to a seventh preferred aspect of the invention one or more electrodes in the electrode array of the invention can be substituted by a group of electrodes temporarily or permanently kept in a fixed relationship in respect of each other, that is, are kept in a fixed relationship in respect of each other; the means for keeping them in the fixed relationship may comprise or consist of one or more matrices of the invention or be independent thereof. If independent from the one or more matrices the means can be one that dissolves and/or disintegrates in aqueous media or a permanent one, such as a means keeping the electrode bundle of WO 2007/040442 in a fixed relationship. Similarly one or more electrodes in the electrode array of the invention can be substituted by electrode bundle(s) of WO 2007/040442.

The electrode array of the invention is suitable for long-lasting stimulation, multi-channel recordings of electrical neuronal activity and levels of transmitter substance through measurements of redox reactions and precise lesions of the tissue for scientific, medical and animal care purposes.

Suitable materials for the matrix portions of the invention are of a biocompatible nature, such as carbohydrate and/or proteinaceous materials. The material selected for the first matrix section preferably has a dissolution rate in a body fluid at a temperature of about 37° C. that allows the distal portions of an electrode to become free, that is, free floating, within a short time, such as within from 1 to 3 minutes. The material selected for the second matrix section is preferably one that has a dissolution or degradation rate in a body fluid at a temperature of about 37° C. that allows the main portions of the electrodes to resist separation for at least 5 min, more preferred for at least 10 min, but in any event for a time that is substantially longer, such as longer by from 1 to 20 min or even longer, than the time required for the distal end portions of the same electrodes to lose restraint by the first matrix section.

According to the invention is also disclosed a method of manufacturing the electrode array by disposing electrodes in parallel in an envelope or sheath having the contour of the distal end portion and the main portion of the electrode array and comprising a proximal opening, consecutively applying solutions or suspensions of the material first and second matrix materials to the electrodes the sheath, evaporating solvent from the solution or suspensions, respectively, in the sheath, and removing the sheath from the electrode array. It is preferred for the sheath to be made of a material that can be easily removed from the electrode array. A preferred material for the sheath is a smooth material of low wettability such as a polyfluorinated hydrocarbon polymer or silicon rubber. It is also preferred for the sheath material to be porous, in particular micro-porous, to facilitate evaporation of solvent.

The invention also relates to the use of the electrode array for long-lasting nerve stimulation, multi-channel recordings of electrical neuronal activity and levels of transmitter substance through measurements of redox reactions and lesions of the tissue for scientific, medical and animal care purposes.

The invention will now be explained in more detail by reference to a number of preferred embodiments illustrated in rough drawing comprising a number of figures, which are however not to scale.

DESCRIPTION OF THE FIGURES

Illustrated is in:

FIG. 15 A prior art electrode (WO 2007/040442) incorporated in a electrode array of the invention, in a partial axial sectional view.

DETAILED DESCRIPTION OF THE INVENTION

Materials and Dimensions

Figure 1:
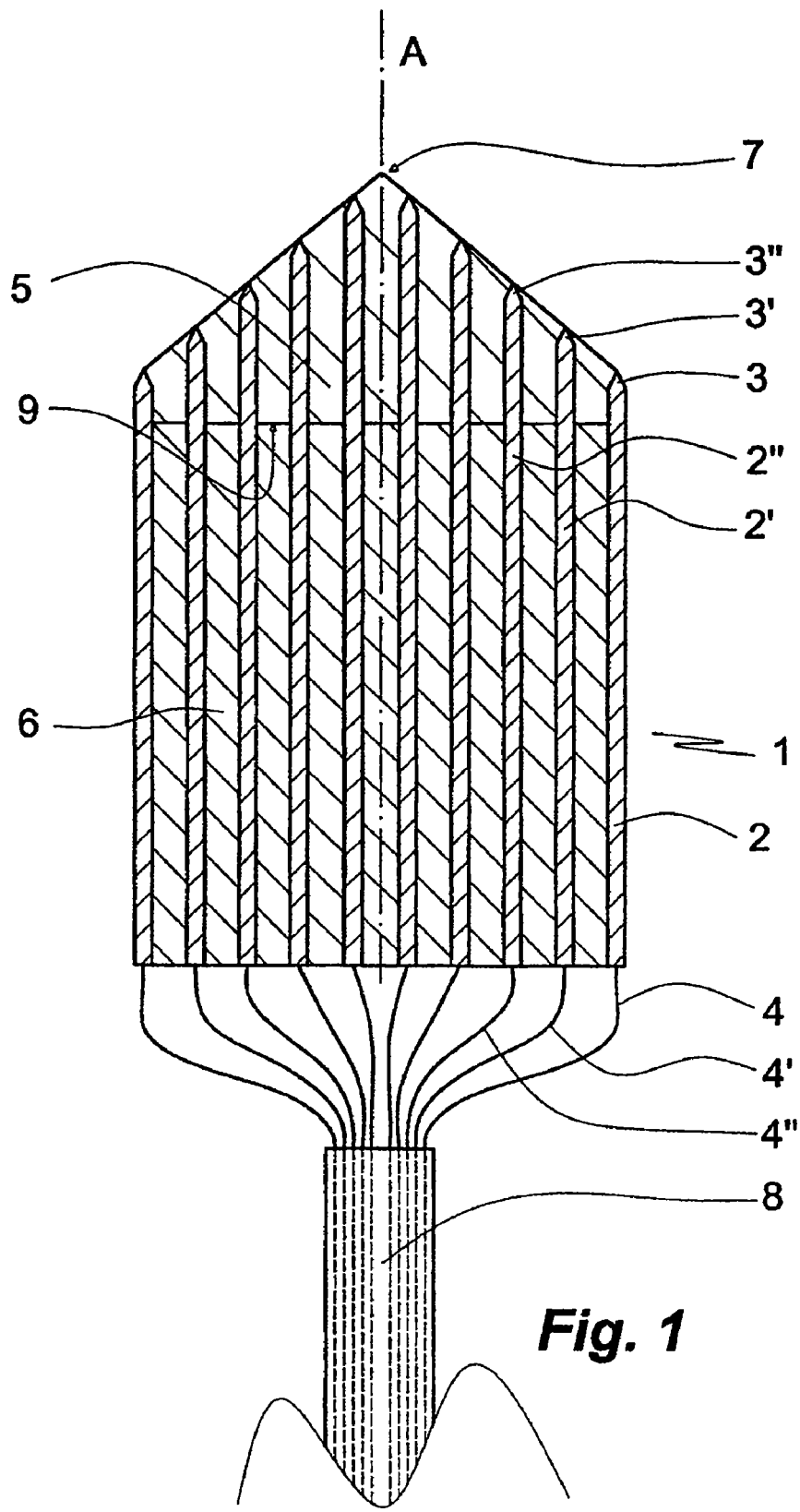
FIG. 1 A first embodiment of the electrode array of the invention comprising a multitude of electrodes embedded in a matrix, in a sectional view.

Electrode materials and dimensions. The electrodes have a suitable diameter of from $10^{-4}$ to $10^{-7}$ m, in particular from 0.5 to 25 µm. Their diameter may change over their length to facilitate insertion into the tissue, in particular the electrode can be tapering towards their distal end. Their distal end can be sharp or blunt but a sharp tip is preferred. Their distal part may even have a diameter smaller than $10^{-7}$. The electrodes comprise an electrically conductive core of a metallic or polymer kind, in particular one of noble metal such as platinum or gold or an alloy comprising more than 30% by weight of noble metal, and an non-conductive coat of, for instance, a polyfluoroalkene, a lacquer, or glass. For electrode cores stainless steel, titanium, and tungsten can also be advantageously used. The electrodes can also be made of a nonconductive supportive material such as glass, ceramic, natural or polymer fiber covered by or, in case of a tubiform supportive material, filled with an electrically conductive material such as a metal, in particular a noble metal or a noble metal alloy. Other examples of useful non-conductive support materials are protein fibers such as silk or carbon such as carbon fibers including fibers comprising carbon nanotubes, which may also be used as a conductive electrode material. The electrically conductive material can be deposited on the support material by conventional sputtering or evaporation techniques.

The surface of electrodes may either be smooth or uneven. An uneven or rugged surface close to the tips is preferred for improving the anchoring properties of the tips. However, other sections of the electrodes may also be given an uneven surface. To further improve the anchoring properties of the electrode array, the electrodes may also be equipped with flexible barbs that stop withdrawal of their withdrawal in a proximal direction. If the barbs are made of electrically conductive material they may also function as electrode tips and, in such case be not insulated.

Matrix materials. Different portions of the electrodes are embedded two or more biocompatible matrix materials; one short lasting material, below referred to as Glue 1, and another longer-lasting material, below referred to as Glue 2. Suitable glue materials include carbohydrate and/or a proteinaceous material. Glue 1 used for embedding a distal end portion of the electrodes has a dissolution rate at a temperature of 37° C. in body fluid such as plasma or interstitial fluid that allows an electrode embedded therein to become unrestrained in regard of its displacement in respect of neighboring electrodes within a short period of time, in particular within 0.5 to 3 minutes. Glue 2 is one that has a dissolution at a temperature of 37° C. in body fluid such as plasma or interstitial fluid that allows an electrode embedded therein to become unrestrained in regard of its displacement in respect of neighboring electrodes within from 1 to 10 minutes or more but in any event for a longer period of time than that required for the distal end portion to become unrestrained in its (lateral) displacement. Longer dissolution times for Glue 1 such as up to 20 minutes and correspondingly longer dissolution times for Glue 2 may be used in the context of a slow insertion procedure, such as an insertion of the corresponding electrode array into very deep tissue.

Suitable materials for Glue 1 include disaccharides such as sucrose that had been boiled in water for 10-30 minutes or longer to yield dissolution times of 1-3 minutes. Boiling for an even longer time produces a glue with a longer dissolution time. Other glues that can be used for Glue 1 include gelatin that had been dissolved in water of 40-50° C. and then allowed to dry.

A suitable material for use as Glue 2 can be obtained by repeated boiling and cooling an aqueous solution containing a sugar or a mixture of sugars selected from sucrose, lactose, mannose, maltose, and an organic acid selected from citric acid, malic acid, phosphoric acid, and tartaric acid. Such glues have a dissolution time in the range of from 13 to 60 min (Erhan et al., 2003, U.S. Pat. No. 6,613,378, incorporated herein by reference).

Various combinations of sugars and organic acids render different dissolution times. Therefore it is also possible to use different combinations differing in dissolution times as Glue 1 and Glue 2. For example, a combination of citric acid with mannose can result in a dissolution time of 13 min, whereas citric acid combined with sucrose can result in a dissolution time of about 30 minutes (U.S. Pat. No. 6,613,378 B1). Hence, these two combinations can be used as Glue 1 and Glue 2, respectively.

Gelatin may also be used both for Glue 1 and for Glue 2. It is well known that different types of gelatin have different dissolution times. Hence, by selecting a proper combination of two different types of gelatin for Glue 1 and Glue 2 it is possible to achieve a faster dissolution time of the distal matrix portion of electrode array (Glue 1) than of the proximal matrix portion of electrode array (Glue 2). The use of a sugar-based glue for the distal matrix portion and of a gelatine-based glue for the proximal matrix portion or vice versa is also possible.

Optionally, glues with substantially longer dissolution times, such as modified collagen, cellulose derivatives, modified starch or other biocompatible materials such as VICRYL™ can also be used as Glue 1 and Glue 2 in applications with a longer insertion procedure. For example, in cases when the track line of the electrode array is assessed repetitively during insertion by, for instance, X-ray imaging, and/or the track line is modified by passing current through contractile filaments comprised by the electrode array, the time for completion of the insertion procedure may take a relatively longer time.

If the electrode array is to be inserted into tissue located immediately below the skin or mucosa or near the surface of the brain or the spinal cord or another tissue, such as to a tissue depth of less than 2 mm, it may suffice to use a single glue, in particular a Glue 1, since only the distal part of the electrode array that is unfolding will be inside the tissue. In this case a Glue 2 disposed between the electrodes of the proximal part of the electrode array will not dissolve due to it retaining its dry state.

Optionally, Glue 2 can be used to hold electrode portions disposed in a central and/or a proximal section of the electrode array, whereas Glue 1 is used to hold electrode portions disposed between their distal ends and the section held by Glue 2. Arranging a centrally axially disposed agent capable of swelling in contact with aqueous media, which additionally is capable of acting as a glue, such as gelatin, provides a separate means for moving/unfolding the electrodes away from the longitudinal axis of the electrode array on contact with body fluid.

Figure 2:
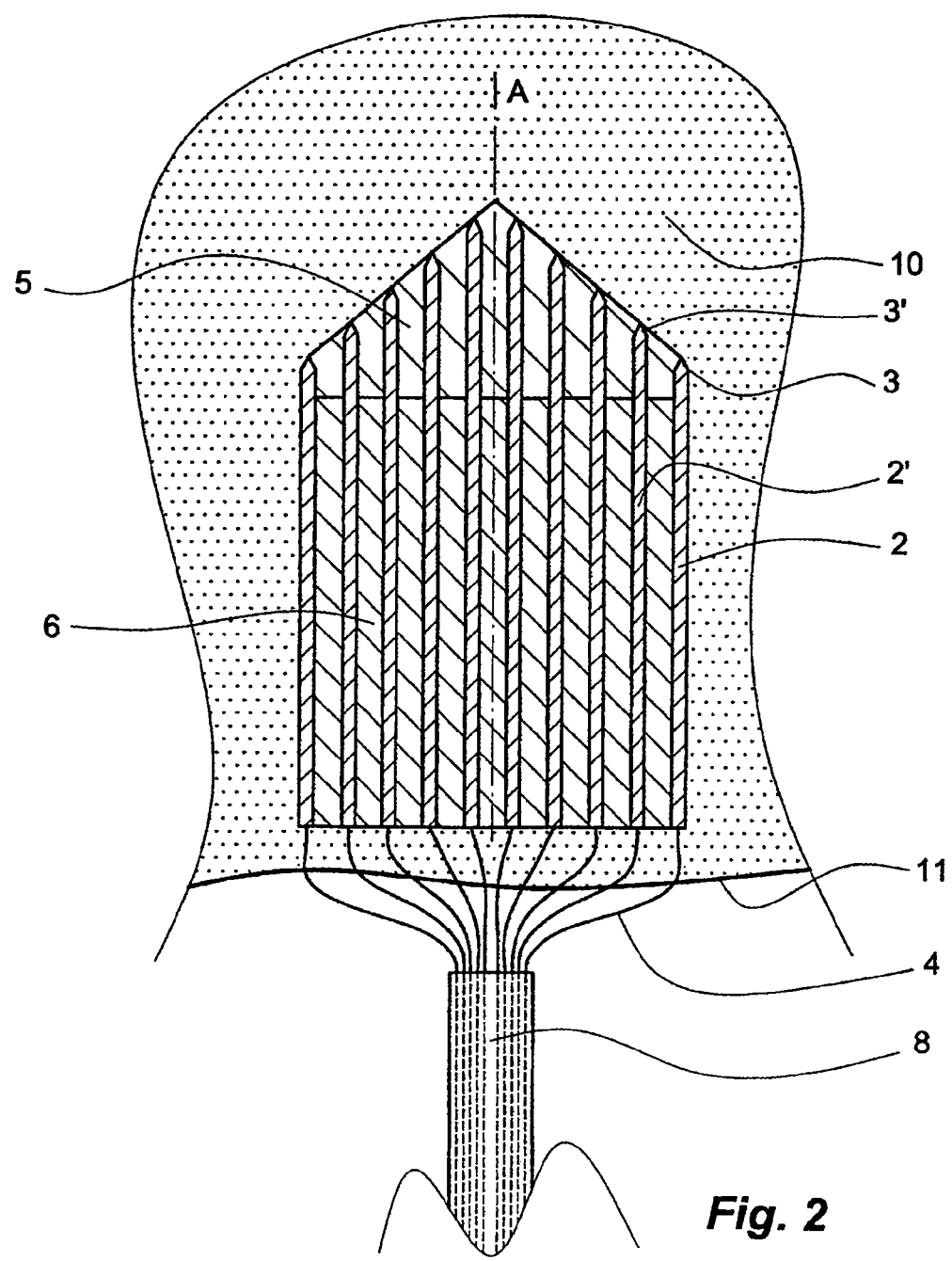
FIG. 2 The embodiment of FIG. 1, immediately upon insertion into soft tissue, in the same view.
Figure 3:
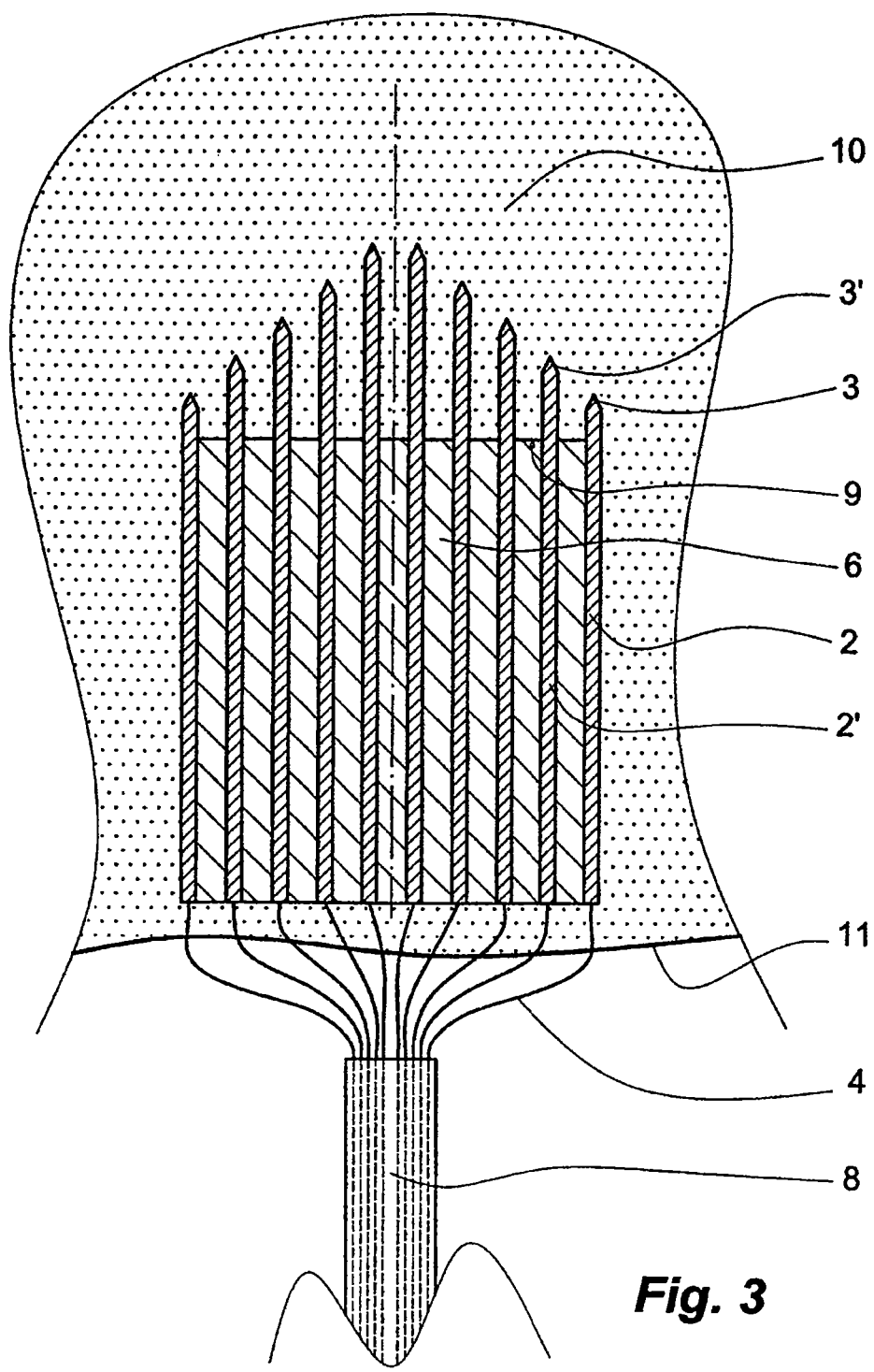
FIG. 3 The embodiment of FIG. 1, inserted into soft tissue for a time sufficient for dissolution of a first matrix section, in the same view.
Figure 4:
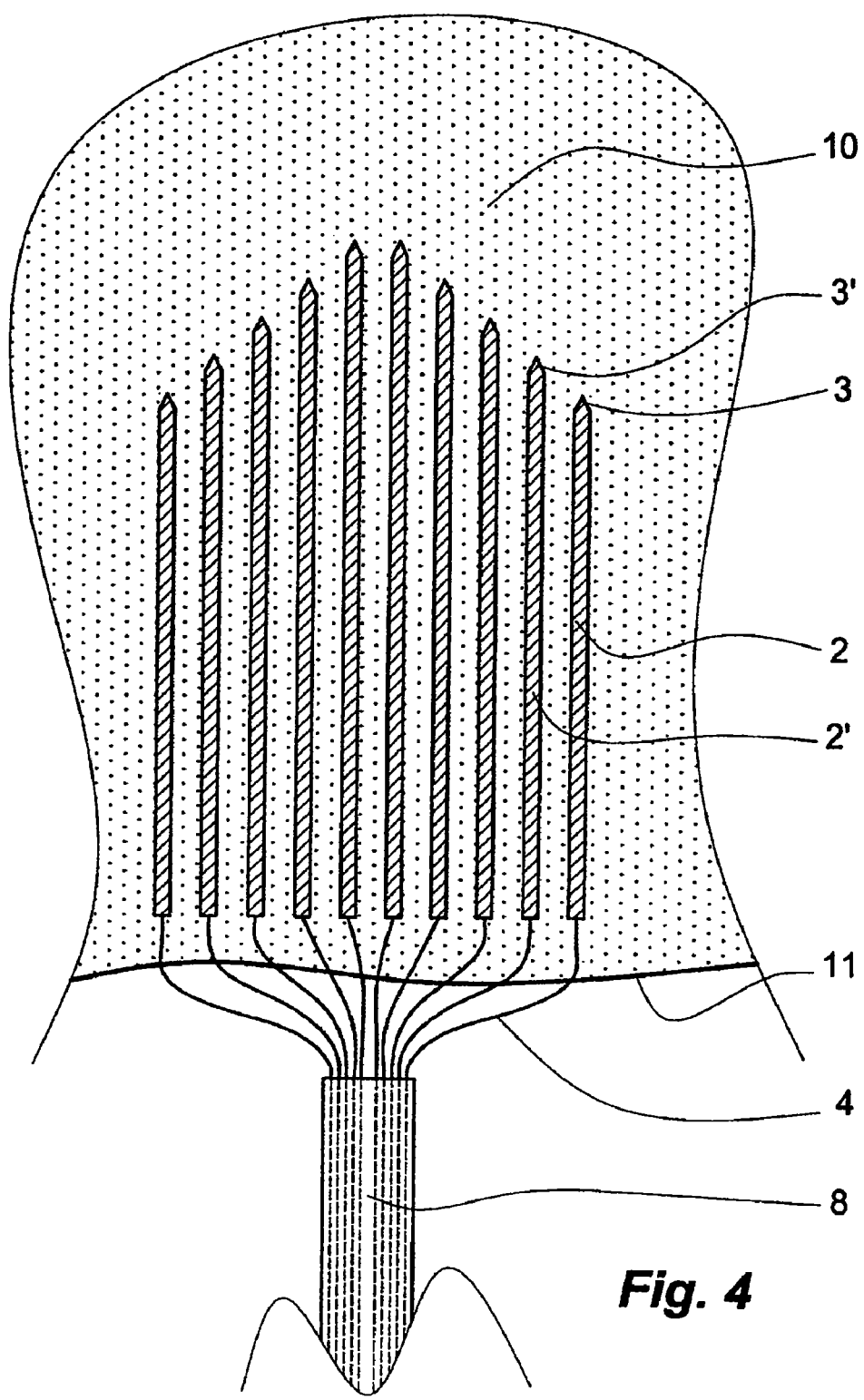
FIG. 4 The embodiment of FIG. 1, inserted into soft tissue for a time sufficient for dissolution of a second matrix section, in the same view.

Optionally the electrode array can be covered by a gliding agent to reduce the friction of electrode array during insertion into the tissue. The gliding agent can also retard the access of body fluid to the glue(s) and thereby the dissolution/degradation thereof Preferred Embodiments The first embodiment 1 of the electrode array of the invention of FIG. 1 comprises a number of thin gold electrodes 2, 2', 2" of varying length disposed in parallel around a central axis A. While the proximal ends of the electrodes 2, 2', 2" are disposed in a plane transverse to the axis A, their distal ends are disposed to form a cone by means of appropriate arrangement taking their varying length into consideration. The distal portions of the electrodes 2, 2', 2" extending from their conical distal tips 3, 3', 3" in a proximal direction are embedded in a first glue matrix 5, which abuts a second glue matrix 6. The interface 9 between the matrices 5, 6 is disposed in a plane transverse to axis A. The tip of the distal cone 7 is comprised by the first glue matrix 5. At its proximal end each electrode 2, 2', 2" is connected to a thin and flexible electrically conductive leads 4, 4', 4", respectively. At a short distance from the electrode array the leads 4, 4', 4" are assembled in a multiple electrode lead line 8 connected to an electronic unit (not shown) for administering electric stimulation through the electrodes 2, 4', 2" and/or for recording electrical signals sensed by the electrodes 2, 2', 2". Except for a short distance extending from their distal tips 3, 3', 3", respectively, the electrodes 2, 2', 2" and their respective leads 4, 4', 4" are insulated (not shown) by a thin layer of polymer lacquer. In contact with water or an aqueous solvent such as a body fluid the first glue matrix 5 dissolves substantially more quickly than the second glue matrix 6. In FIG. 2 the electrode array 1 is shown inserted into soft tissue 10, the surface of which is designated by reference no. 11 to a depth making only the leads 4, 4', 4" and the multiple electrode lead line 8 extend from the tissue 10. The state of the electrode array 1 in FIG. 2 is immediate upon insertion. After a short period of time such as about a minute, the state of the electrode array 1 shown in FIG. 3 is reached. The first glue 5 has dissolved in the aqueous interstitial fluid of the tissue 10. Distal end portions of the electrodes 2, 2', etc. are now unrestrained in their lateral movement, in particular at their tips 3, 3'. The proximal portions of the electrodes 2, 2', etc. are however still embedded in the second glue matrix 6, which only dissolves so slowly that even a radially outermost disposed electrode 3 remains embedded in the second glue matrix 6 until the first glue matrix 5 has fully dissolved. The dissolution of the second glue matrix 6 consumes at least 10 minutes; at its end the state shown in FIG. 4 is reached, in which each electrode 2, 2' is capable of axial or lateral movement in the tissue 10 unimpeded by neighboring electrodes 2' and 2, respectively.

Figure 5:
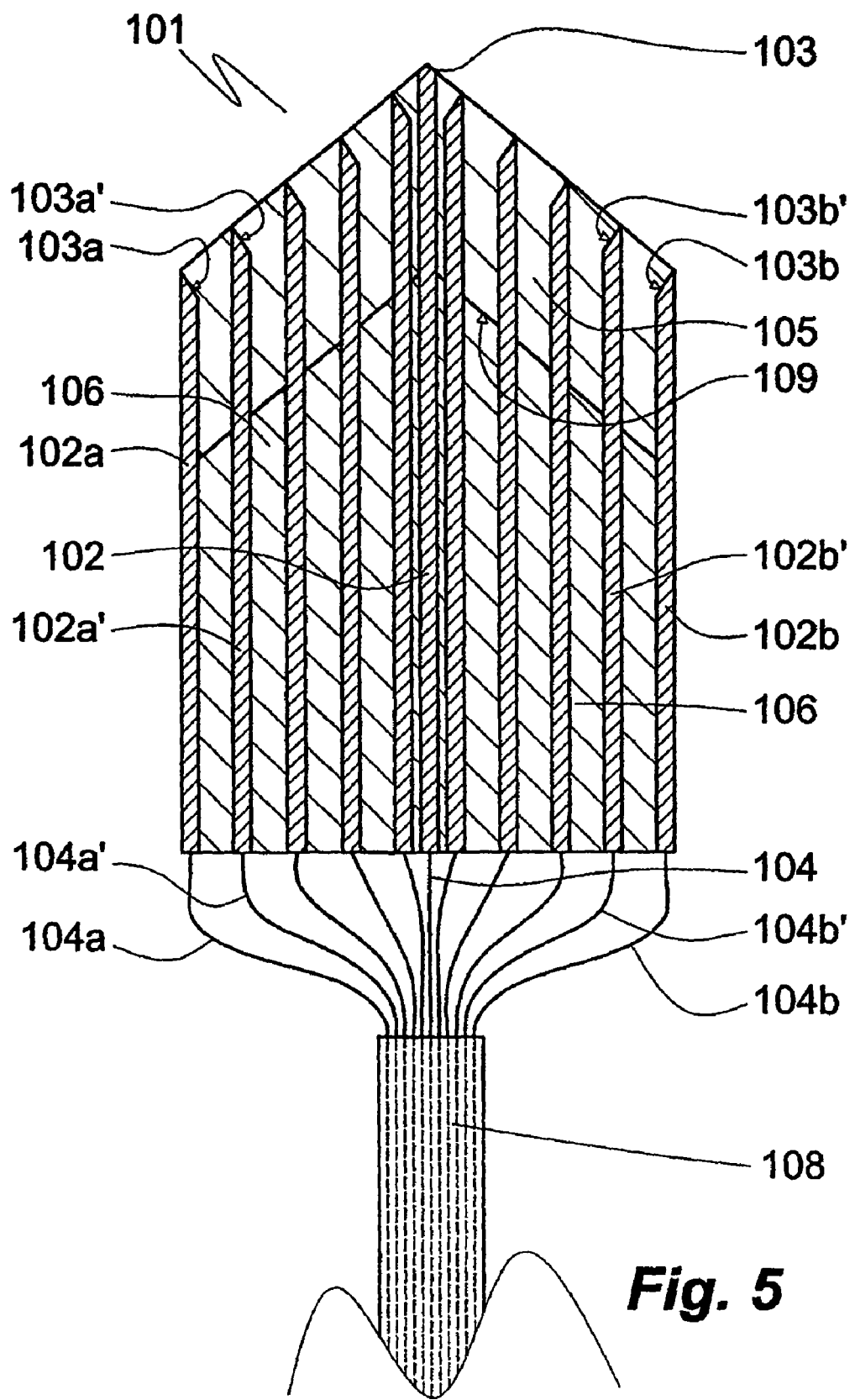
FIG. 5 A second embodiment of the electrode array of the invention in the same view as the embodiment of FIG. 1.

The second embodiment of the electrode array 101 of the invention shown in FIG. 5 differs from the embodiment of FIG. 1 in that it comprises two kinds of electrodes, a centrally disposed electrode 102 with a conical distal tip 103 around which lateral electrodes 102a, 102a'; 102b, 102b' of varying lengths having tips 103a, 103a'; 103b, 103b' at their distal ends slanting in a radial direction are disposed symmetrically. At their proximal ends each electrode 102; 102a, 102a'; 102b, 102b' is connected to a thin flexible electrically conduction lead 104; 104a, 104a'; 104b, 104b', respectively, which are combined at a short distance from the proximal end of the electrode array 101 in a multiple electrode lead line 108 of same function as the multiple electrode lead line 8 of the first embodiment. Again, distal portions of the electrodes 102; 102a, 102a'; 102b, 102b' are embedded in a first matrix glue 105 extending to a cone-formed interface 109 with a second matrix glue 106 extending to their proximal ends. The first and second matrix glues 105, 106 are of the same kind as the glues 5, 6 of the first embodiment. In contrast to the first embodiment the distal tip 103 of the distal cone of the electrode array 101 is formed by the tip of an electrode, that is, the tip 103 of the central electrode 102. The function of the slanting tips 103a, 103a'; 103b, 103b' is explained below in connection with a third embodiment of the electrode array of the invention.

Figure 6:
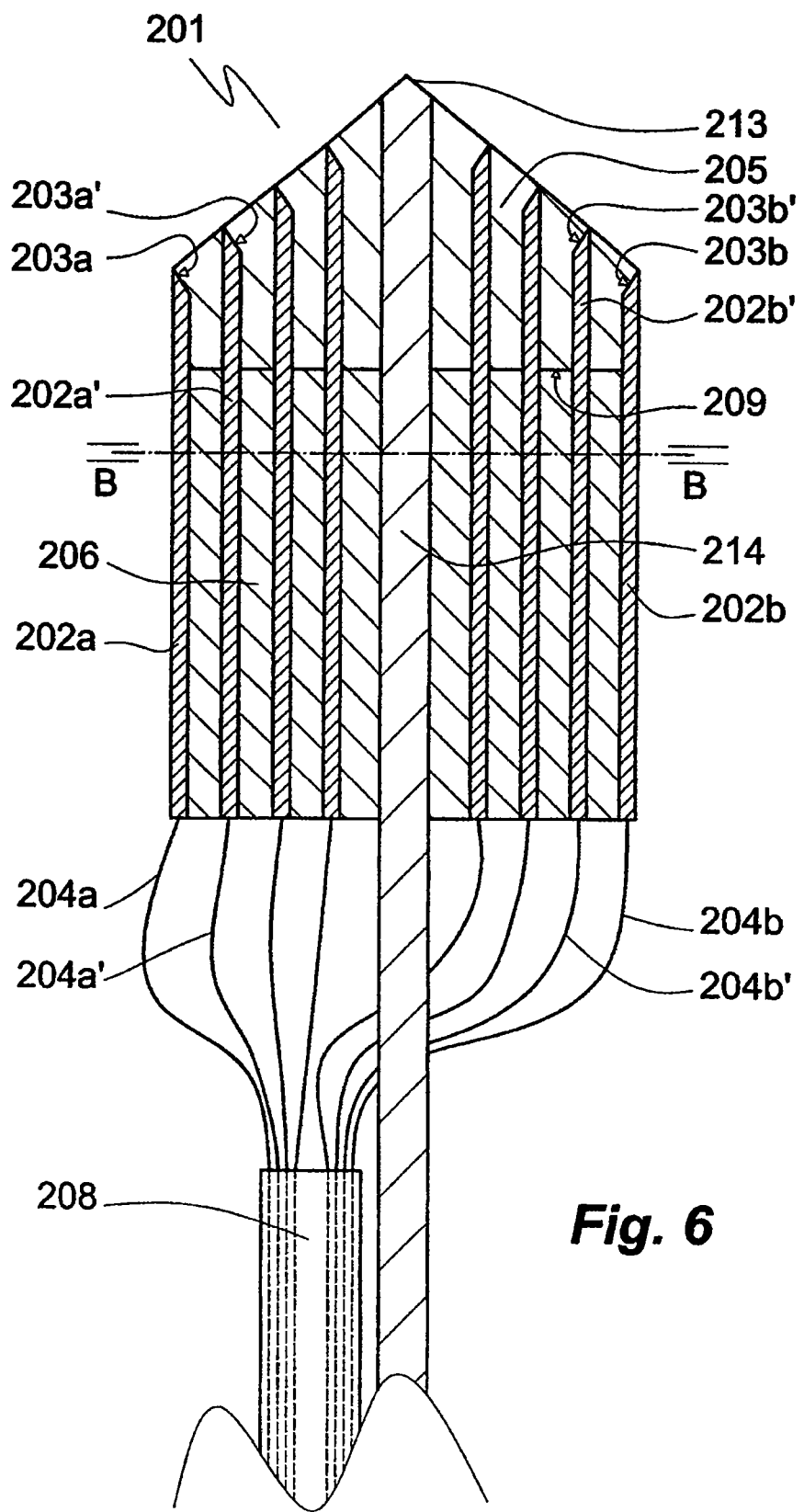
FIG. 6 A third embodiment of the electrode array of the invention comprising an insertion guide element, in the same view as the embodiment in FIG. 1 (section C-C, FIG. 9)
Figure 7:
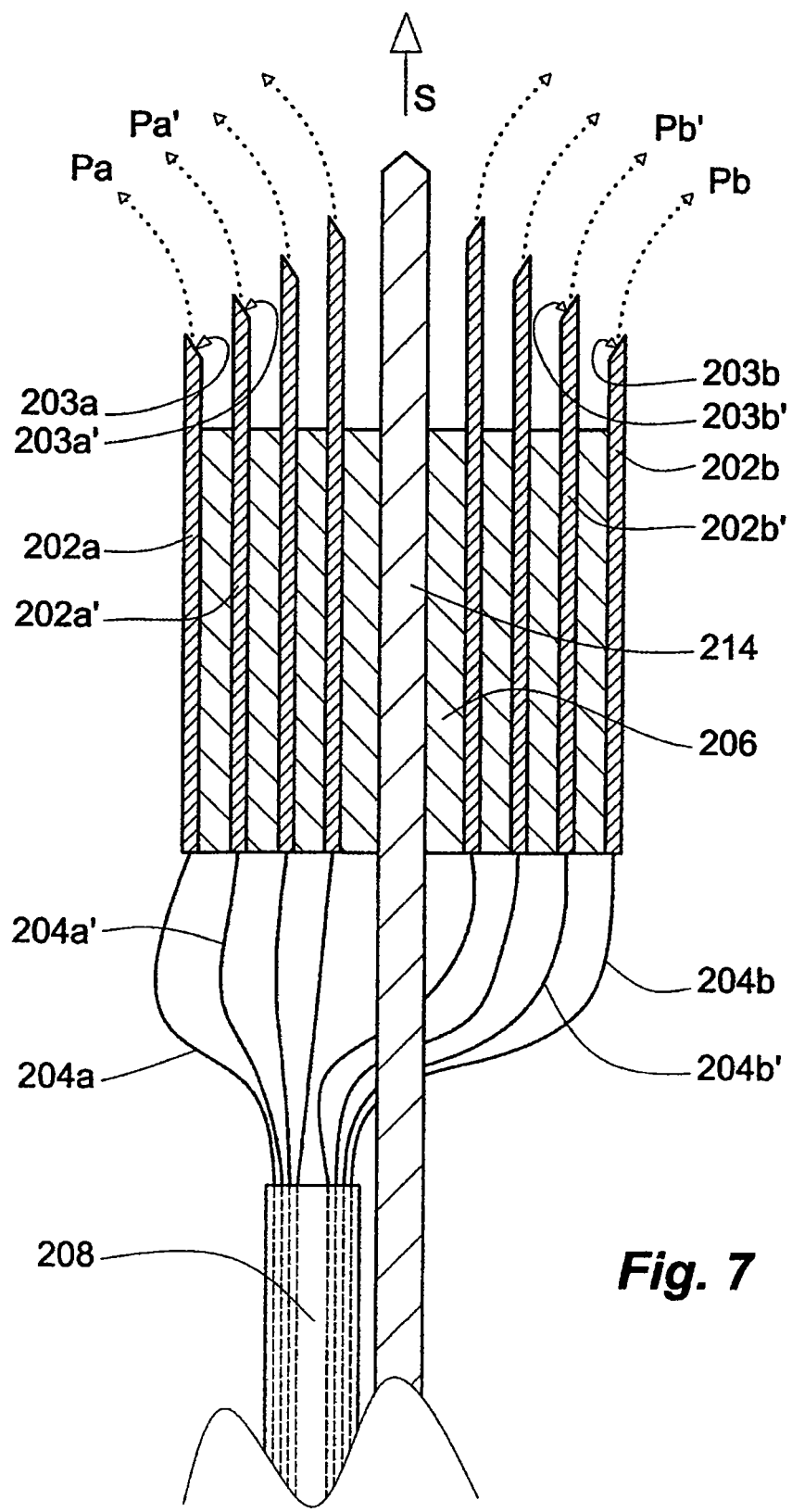
FIG. 7 The embodiment of FIG. 6, inserted into soft tissue for a time sufficient for dissolution of a first matrix section, in the same view.
Figure 9:
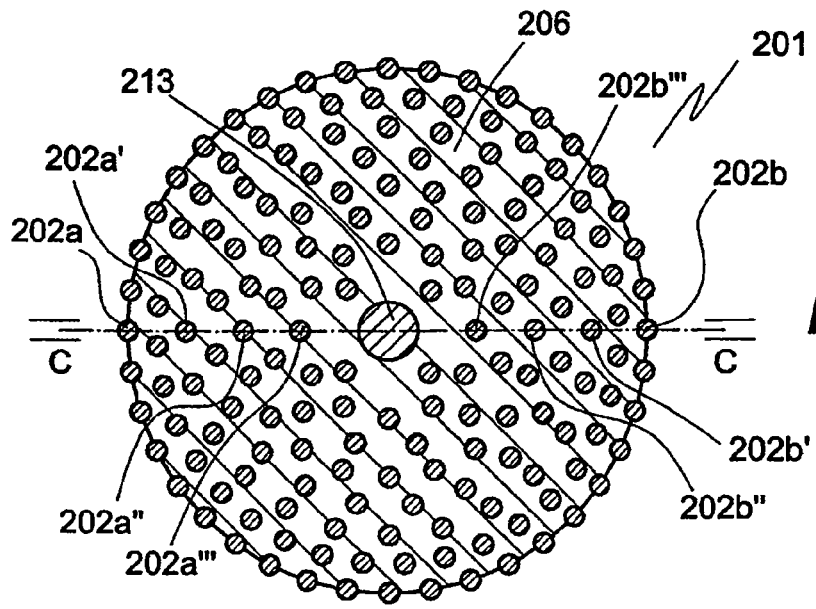
FIG. 9 A transverse section B-B through the embodiment of FIG. 6.

The third embodiment of the electrode array 201 of the invention shown in FIGS. 6 and 9 differs from the embodiment of FIG. 5 in that the central electrode 103 has been exchanged for insertion rod 214 ending in a conical distal tip 213. The insertion rod 213 extends from the proximal end of the electrode array 201 with a length suitable for manual handing of the electrode array 201 during insertion into soft tissue. Electrodes 202a, 202a'; 202b, 202b' of varying length having tips 203a, 203a'; 203b, 203b' at their distal ends slanting in a radial direction are disposed symmetrically around the insertion rod 214. At their proximal ends each electrode 202a; 202a'; 202b, 202b' is connected to a thin flexible electrically conduction lead 204a, 204a'; 204b, 204b', respectively, which leads are combined at a short distance from the proximal end of the electrode array 201 in a multiple electrode lead line 208 of same function as the cable 8 of the first embodiment. Again, distal portions of the electrodes 202a, 202a'; 202b, 202b' are embedded in a first matrix glue 205 extending to an interface 209 with a second matrix glue 206 extending to their proximal ends. The first and second matrix glues 205, 206 are of the same kind as the glues 5, 6 of the first embodiment. The distal cone of the electrode array 201 is formed by the tip 213 of the insertion rod 214. The function of the slanting tips 203a, 203a'; 203b, 203b' is evident from FIG. 7, in which the first matrix glue of the electrode array 201 has been dissolved, whereas the second matrix glue still holds proximal portions of the electrodes 202a, 202a'; 202b, 202b' embedded. Distal end portions of the electrodes 202a, 202a'; 202b, 202b' comprising the slanting tips 203a, 203a'; 203b, 203b', respectively are now no longer restrained in their lateral movement. Pushing the electrode array 201 further into soft tissue (not shown in FIG. 7) in the direction indicated by arrow S will deflect the slanting tips 203a, 203a'; 203b, 203b' outwardly, that is, in a direction away from the central insertion rod 214, as indicated by dotted arrows $P_a$, $P_{a'}$ and $P_b$, $P_{b'}$. The slanting electrode tips 203a, 203a'; 203b, 203b' thus provide an unfolding means for the respective electrodes 202a, 202a'; 202b, 202b' and an anchoring means for the electrode array 201. As before, each electrode 202a, 202a'; 202b, 202b' is connected to a thin electrically conducting lead 204a, 204a'; 204b, 204b', respectively, which leads are combined in a multiple electrode lead line 208.

Figure 8:
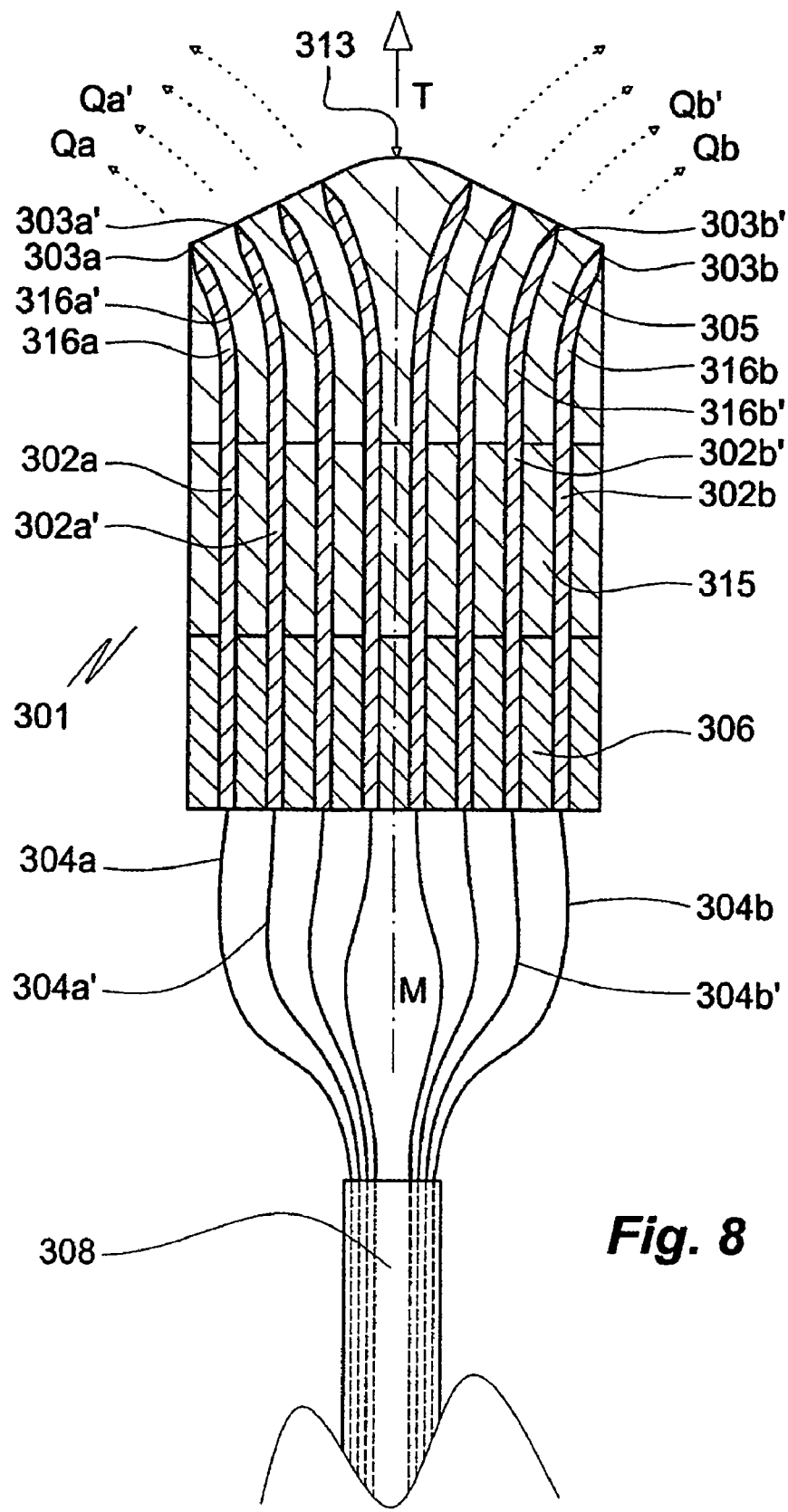
FIG. 8 A fourth embodiment of the electrode array of the invention, in the same view as the embodiment of FIG. 1.

The fourth embodiment of the electrode array 301 of the invention shown in FIG. 8 differs from the embodiment of FIG. 1 in that the electrodes 302a, 302a'; 302b, 302b' of varying length and provided with conical tips 303a; 303a'; 303b, 303b' have distal terminal sections 316a, 316a'; 316b, 316' bent away radially from the central axis M of the electrode array 303. At its proximal end each electrode 302a; 302a'; 302b, 302b' is connected to a thin flexible electrically conduction lead 304a, 304a'; 304b, 304b', respectively, which leads are combined at a short distance from the proximal end of the electrode array 301 in a multiple electrode lead line 308 of same function as the cable 8 of the first embodiment. Again, distal portions of the electrodes 302a, 302a'; 302b, 302b' are embedded in a first matrix glue section 305. Portions of the electrodes 302a, 302a'; 302b, 302b' extending from their proximal ends are embedded in a second matrix glue section 306, which however does not extend to the first matrix glue section 305. Instead, a third matrix glue section 315 is disposed between glue sections 305 and 306. The dissolution properties of the third matrix glue section 315 is similar to that of the second matrix glue section 306 but, in addition, the third matrix glue section 315 does swell before dissolving, thereby pushing the distal portions 316a, 316a'; 316b, 316' of the electrodes 302a, 302a'; 302b, 302b' further radially outwards. The first and second matrix glues 305, 306 are of the same kind as the glues 5, 6 of the first embodiment. The distal cone of the electrode array 301 has a rounded tip 313 comprised by the first matrix portion 305. The bent configuration of the distal end section of the electrodes 302a, 302a'; 302b, 302b' controls their unfolding along paths $Q_a$, $Q_{a'}$, and $Q_b$, $Q_{b'}$ upon dissolution of the first glue matrix 306 and pushing of the electrode array 301 in a proximal direction indicated by arrow T. Again, each electrode 302a, 302a'; 302b, 302b' is connected to a thin electrically conducting lead 304a, 304a'; 304b, 304b', respectively, which leads are combined in a multiple electrode lead line 308.

Transverse sections through other preferred embodiments are shown in FIGS. 10 to 13.

Figure 10:
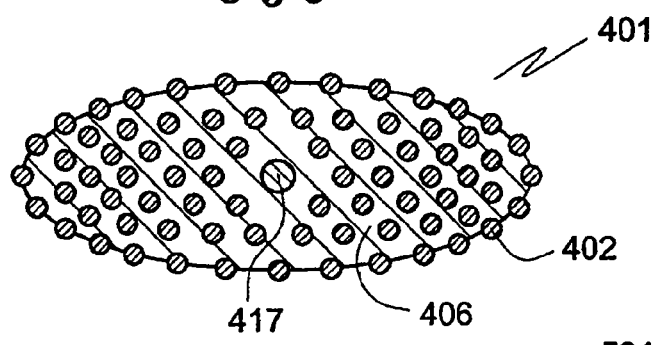
FIG. 10 A fifth embodiment of the invention, in a transverse section corresponding to that of FIG. 9.

The fifth embodiment of the electrode array 401 of the invention illustrated in FIG. 10 is elliptical in a transverse section. A multitude of thin flexible electrodes 402 are disposed around a central optical fiber 417, by which radiation can be conducted to a tissue site of interest; optionally radiation reflected from the tissue can be adduced to a radiation recording instrument such as an IR-instrument (not shown). The electrodes 402 are embedded in first and second 406 glue matrix sections. In addition the electrode array 401 shares principal design features of the aforementioned embodiments of the invention.

Figure 11:
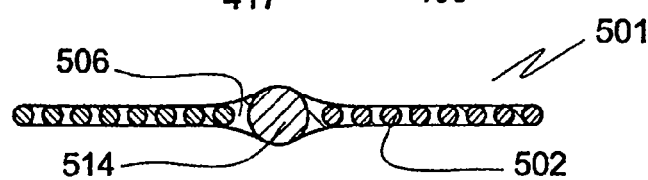
FIG. 11 A sixth embodiment of the invention, in a transverse section corresponding to that of FIG. 9.

The sixth embodiment of the electrode array 501 of the invention illustrated in FIG. 11 is of a flat design and similar to the embodiment of FIG. 1 in an axial section. It comprises a central insertion rod 514 from which wings comprising thin flexible electrodes 502 embedded in first and second 506 glue matrices extend. In addition the electrode array 501 shares principal design features of aforementioned embodiments of the invention.

Figure 12:
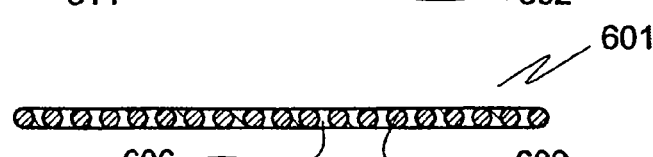
FIG. 12 A seventh embodiment of the invention, in a transverse section corresponding to that of FIG. 9.

The seventh embodiment of the electrode array 601 of the invention illustrated in FIG. 12 is of a similar design as the fifth embodiment of the invention; it lacks however a central insertion rod. It comprises thin flexible electrodes 602 embedded in first and second 606 glue matrices. In addition the electrode array 601 shares principal design features of aforementioned embodiments of the invention.

Figure 13:
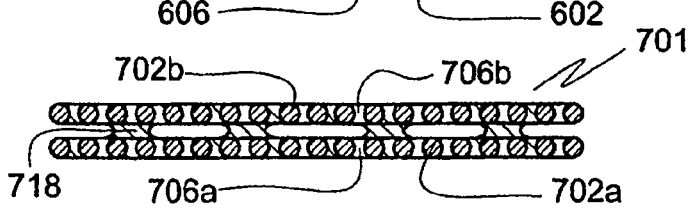
FIG. 13 An eight embodiment of the invention, in a transverse section corresponding to that of FIG. 9.

The eight embodiment of the electrode array 701 of the invention illustrated in FIG. 13 is a combination of two flat electrode arrays of identical shape, each corresponding to an electrode array of the seventh embodiment, with their flat faces superimposed and joined by spaced glue sections 718. Their electrodes have reference numbers 702a, 702b, and their second glue sections in which they are shown imbedded have reference numbers 706a, 706b, respectively.

Figure 14:
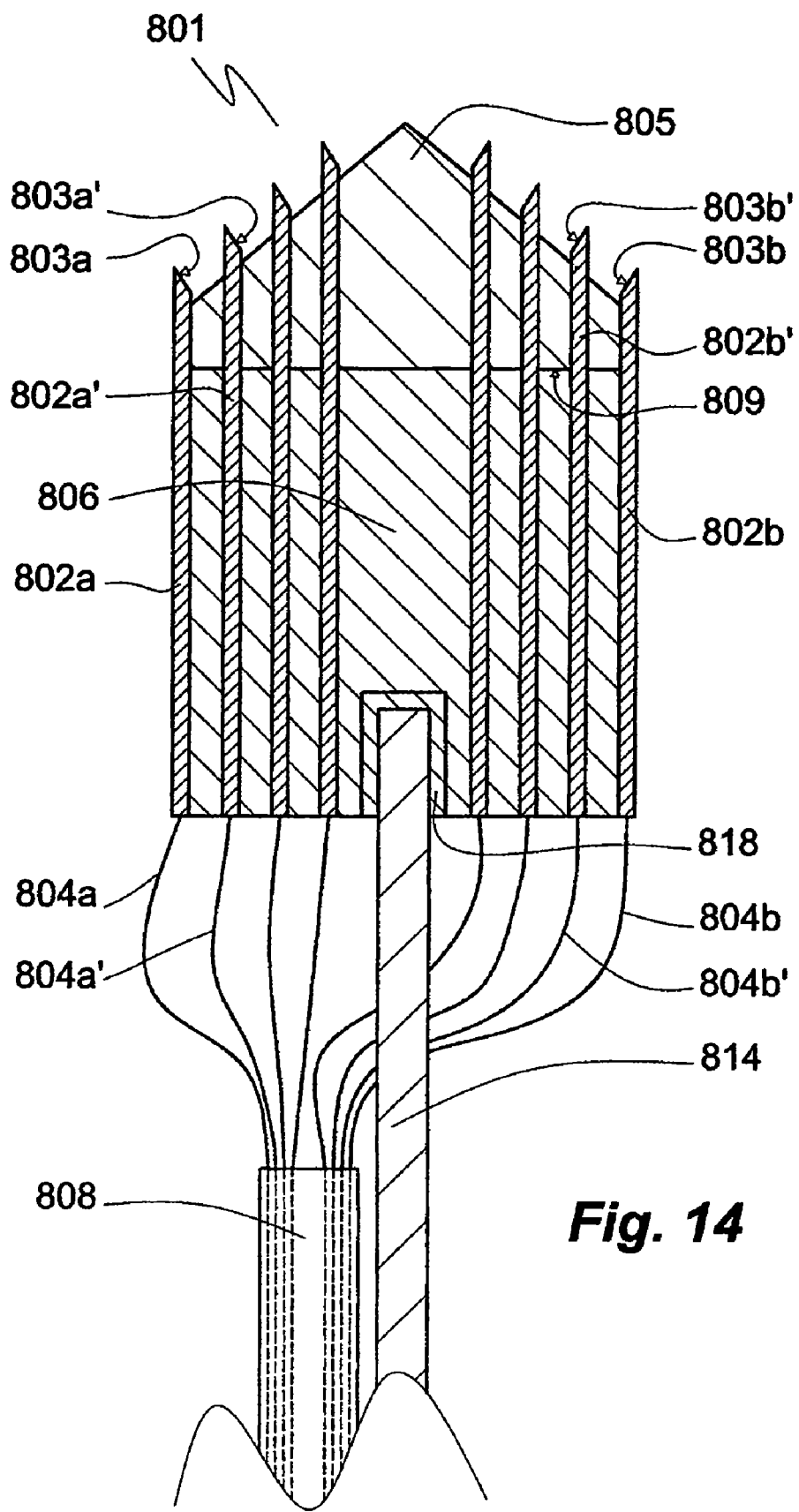
FIG. 14 A ninth embodiment of the invention, in a transverse section corresponding to that of FIG. 6.

The ninth embodiment of the electrode array 801 shown in FIG. 14 corresponds to the embodiment of FIG. 6 except for the electrode tips 803a, 803a'; 803b, 803b' not being imbedded in a first matrix glue 805 (from which they thus extend), and by the insertion rod 814 not extending through the entire electrode array to its distal end. Instead the insertion rod 814 is mounted in a central cylindrical axial pocket in flat proximal face of the second glue matrix section 806 electrode array by means of a glue 818. The dissolution rate of the glue 818 in an aqueous environment is substantially higher than the dissolution rate of the second glue matrix section 806. The electrodes 802a, 802a'; 802b, 802b' have tips 803a, 803a'; 803b, 803b' slanting in a proximal direction towards the central axis of the electrode array 801 (not indicated). Their distal portions are embedded in a first matrix glue section 805 of a higher dissolution rate in aqueous media than that of the second matrix glue section 806 in which their proximal portions that are embedded. The interface 809 between the first and second glue matrix sections is disposed proximally of the conical distal portion of the electrode array 801. To the proximal end of each electrode 802a, 802a'; 802b, 802b' is attached a thin flexible electrically conducting lead 804a, 804a'; 804b, 804b', respectively; at a short distance from the proximal end of the electrode array 801 the leads are 804a, 804a'; 804b, 804b' are combined in a multiple electrode lead line 808.

A prior art electrode 902 (FIGS. 15, 15a) incorporated in an electrode array 901 of the invention comprises a barb 920 that ends in a sharp point 921 extending in a proximal direction from blunt electrode tip 903. The barb 920 is integral with the electrode 902, which is manufactured from very thin metal wire. Except for the barb 920 and its tip 921 (pointed hatch sections in FIGS. 15, 15a) the electrode 902 is insulated by a thin layer of polymer (not shown). In FIG. 15 the curved barb 209 is kept in resilient abutment with the electrode 902 by embedment in a first glue matrix 905. The proximal part of the electrode comprises a terminal proximal section of the electrode 902 embedded in a second glue matrix 906. To the short proximal terminal portion of the electrode 902 extending from the second glue matrix 906 a thin wire lead 904 is soldered at 925. At a short distance from the soldering point 925 a micro-signalamplifier 926 is integral with the lead 904. Upon dissolution of the first glue matrix 905 the barb 902 is no longer restricted in its movement, and assumes its physically unrestricted bent configuration shown in FIG. 15a. The proximal end of the electrode 902 however still remains embedded in the second glue matrix 906.

Applications of the Electrode Array of the Invention

The EA of the invention is primarily intended for treatment of human with pain, epilepsy, depression, injuries or degeneration in the brain and/or the spinal cord; as an interface in brain-computer communication enabling prosthesis control or control of skeletal muscle; for control of endocrine and exocrine organ function; and as a research tool in studies of neuronal network function, and plasticity, development and aging of the nervous system.

Clinical use of the electrode array of the invention may particularly serve to aid patients with brain or spinal damage of various kind by recording signals from remaining neurons in case of, e.g., stroke or degenerative disease and/or to stimulate neurons to compensate for lost functions. Similar uses are possible in animals. For instance, the electrode array can be used to relieve pain by stimulation of analgesic brain stem centers, such as nuclei in the periaqueductal grey substance; to relieve or decrease tremor in Parkinson's disease, choreatic and other involuntary movements by stimulation within the basal ganglia or associated nuclei; to boost memory by stimulation of cholinergic and/or monoaminergic nuclei in case of Alzheimer's disease or other degenerative diseases; to control mood, aggression, depression, anxiety, phobia, affect, sexual over-activity, impotence, eating disturbances by stimulation of limbic centers or other brain areas; to rehabilitate patients after stroke or damage of the brain/spinal cord by stimulation of remaining connections in cortex cerebri or descending motor pathways; to re-establish control of spinal functions such as bladder and bowel emptying after spinal cord injury by stimulating relevant parts in the spinal cord; to control spasticity by stimulation of inhibitory supraspinal descending centers or appropriate cerebellar areas. DMCE can also be used to induce sleep in patients suffering from insomnia.

The electrode array of the invention may be used for electrolytic lesioning of specific tissue sites by passing electrical currents through the tissue. Current of a suitable strength can also be used to heat the electrode filaments and thereby increase the temperature to a level at which neighboring cells are killed. In such case the intensity of the current administered via the electrode bundle is chosen to be adequate for accomplishing cell death in a tissue volume adjacent to the front end of the electrode bundle. For example, the electrode array can be used to lesion tumors or CNS sites that developed abnormal activity after e.g. an insult or a degenerative disease.

Examples of combined recording and stimulation include: monitoring of epileptic attacks by electrodes implanted into the epileptic focus coupled with a system for administration of antiepileptic drugs and/or electrical pulses; compensating for lost connections in the motor system by recording central motor commands, and stimulating the executive parts of the motor system distal of the lesions; selecting a site producing abnormal electrical activity by recording neuronal activity at the site, followed by lesioning the tissue at the site by administration via the electrode bundle of a current of adequate strength for an adequate period of time.

The electrode array of the invention can also serve as an interface for communication with computers and neuroprostheses. In patients with damages to the peripheral nervous system, it can be useful to record command signals from the CNS. These signals can be interpreted by computer programs and used to control neuroprostheses such as artificial hands or feet, and also to control stimulation of muscles and organs such as the bladder and the bowel.

Furthermore, the electrode array of the invention may be used to measure the activity and to control the secretion of hormones from exocrine or endocrine organs, in patients with deficient hormone secretion or regulation The use of the electrode array of the invention for studies of normal as well as abnormal functions of the brain and the spinal cord can include, for instance, monitoring pain related neuronal activity, for example in the primary somatosensory cortex or in the limbic system, thereby enabling assessments of the potency of potentially analgesic compounds or analgesic treatments. Another example is the monitoring of epileptic activity in animals to test the efficacy of antiepileptic compounds or treatments. Further examples include recordings of activity in neuronal centers that regulate sleep to study sleep disorders, and recordings of neuronal centers that regulate appetite to study problems related to obesity. In such studies it is necessary to record neuronal activity and to simultaneously interact with the undisturbed central nervous system. For this purpose, the electrode array of the invention is implanted in the CNS for a long time. It can also be used as a carrier for biosensors that measure, for instance, the concentration levels of various molecules in the tissue.

If equipped with optical fibers the electrode array of the invention can be used to mediate signals from fluophores introduced in the cells by, for example knock-in gene techniques.

A person skilled in the art will appreciate that the embodiments and uses of the electrode array of the invention disclosed herein are only given for exemplification. He or she will also appreciate that mere combinations of the features of the various embodiments other than those specifically described herein also comprised by the invention.

The invention claimed is:

1. Electrode array for insertion into soft tissue of an animal including man comprising a multitude of thin flexible electrodes each having a distal tip and a proximal end, wherein at least portions of the electrodes extending from their proximal ends are disposed in parallel, a matrix dissolvable in an aqueous body fluid of the animal, the electrodes being embedded in the matrix, wherein the matrix comprises first and second sections differing in their dissolution rates, the first section enclosing a portion of the electrodes extending from a distal portion of the electrodes in a proximal direction to an end position distant from the proximal ends of the electrodes, and the second section enclosing a portion of the electrodes extending from the first section end position towards the proximal ends of the electrodes.

2. The electrode array of claim 1, wherein the dissolution rate of the first matrix portion is higher than the dissolution rate of the second matrix portion.

3. The electrode array of claim 2, further comprising a plurality of flexible leads, and each flexible lead is electrically conducting attached to the proximal end of an electrode of the multitude of electrodes.

4. The electrode array of claim 3, further comprising insulation associated with each electrode such that the electrode is electrically insulated except at-the distal end thereof.

5. The electrode array of claim 4, wherein the electrodes are of different length.

6. The electrode array of claim 5, wherein the electrodes are disposed around an axis with their distal ends in a plane transverse to the axis and in a manner of their length increasing towards the axis.

7. The electrode array of claim 6, wherein the distal portions of the electrodes define a cone or a symmetric axial section of a cone.

8. The electrode array of claim 1, wherein the distal portions of the electrodes comprise unfolding means, and wherein the electrodes have a central axis.

9. The electrode array of claim 8, wherein the distal tips of the electrodes are unilaterally slanting in a proximal direction towards the electrode central axis.

10. The electrode array of claim 8, wherein electrode sections extending from the distal tips are bent away from the central axis.

11. The electrode array of claim 8, wherein electrode sections extending from the distal tips are disposed in the first matrix section in a resiliently restrained manner so as to allow them to bend away from the central axis on dissolution of the first matrix section.

12. The electrode array of claim 1, wherein the dissolution rate of the first matrix portion is sufficient to make the first matrix portion substantially dissolve in a body fluid before the second matrix portion is dissolved to an extent sufficient for electrodes embedded therein to lose their embedment.

13. The electrode array of claim 1, further comprising an agent disposed between the electrodes thereof capable of swelling in an aqueous solvent.

14. The electrode array of claim 1, further comprising one or more optical fibers in electrical contact with a proximal end of one or more of the electrodes.

15. The electrode array of claim 1, further comprising one or more contractile polymer elements disposed for controlling the path of insertion of the electrode array.

16. The electrode array of claim 1, further comprising a micro-amplifier, wherein an electrode is connected to the micro-amplifier in the vicinity of the proximal end of the electrode.

17. The electrode array of claim 1, wherein each of the first and second sections encase the portions of the electrodes embedded in the respective sections.

18. The electrode array of claim 17, wherein the electrodes are disposed around a common axis.

19. The electrode array of claim 18, further comprising a plurality of flexible leads, and each flexible lead is electrically conducting attached to the proximal end of an electrode of the multitude of electrodes.

* * * * *